United States Patent [19]
Russell

[11] 3,991,790
[45] Nov. 16, 1976

[54] PATIENT VENTILATOR TRIGGER CIRCUIT

[75] Inventor: George K. Russell, Castle Rock, Colo.

[73] Assignee: Sandoz, Inc., E. Hanover, N.J.

[22] Filed: June 26, 1975

[21] Appl. No.: 590,616

Related U.S. Application Data

[62] Division of Ser. No. 401,739, Sept. 28, 1973, Pat. No. 3,916,889.

[52] U.S. Cl. ................................................ 137/819
[51] Int. Cl.² ............................................... F15C 1/12
[58] Field of Search ............................ 137/819, 821; 128/145.8

[56] References Cited
UNITED STATES PATENTS

| | | |
|---|---|---|
| 3,429,248 | 2/1969 | Furlong ........................ 137/819 X |
| 3,587,609 | 6/1971 | DiCamillo .................... 137/819 X |
| 3,631,874 | 2/1972 | Rexford ........................ 137/821 X |

Primary Examiner—William R. Cline
Attorney, Agent, or Firm—Gerald D. Sharkin; Robert S. Honor; Walter F. Jewell

[57] ABSTRACT

Disclosed herein is a patient ventilator apparatus having a pneumatic control system operable in three different modes wherein the apparatus assists the breathing of the patient, controls the patient's breathing in a timed manner, or operates in a combination assist-/control mode according to certain predetermined conditions. Fluidic circuitry controls a valved bellows apparatus, which in turn supplies air to a patient subject to limitations of time, volume, and pressure, wherein the gas supplied to the bellows comprises an adjustable oxygen/air mixture. Fluidic timers are provided for use in the control mode of the circuitry, and identical fluidic circuitry combinations are provided for use in the assist mode to automatically trigger the ventilator apparatus into an inspiratory state according to the patient's breathing requirements and to trigger such apparatus into an exhalation state when a predetermined inspiratory pressure is attained.

1 Claim, 9 Drawing Figures

PATIENT VENTILATOR TRIGGER CIRCUIT

This application is a divisional application of Ser. No. 401,739, filed Sept. 28, 1973, now U.S. Pat. No. 3,916,889.

BACKGROUND OF THE DISCLOSURE

Certain respiratory apparatus is known in the art wherein fluidic circuits are provided for controlling the exhalation and inhalation cycles of a patient. However, the instant disclosure relates to an improved patient ventilator apparatus utilizing totally pneumatic control circuitry for operating the ventilator apparatus in a plurality of desired modes wherein the breathing of the patient is assisted, completely controlled, or subjected to a combination assist/control operation according to predetermined parameters.

SUMMARY OF THE INVENTION

In accordance with the invention there is provided a pneumatic ventilator apparatus utilizing a pressurized source of gas for operating fluidic circuitry, which in turn controls a source of gas supplied to a patient. During the inspiratory cycle air is exhausted from a bellows apparatus, and supplied through an outlet valve to a patient breathing hose. The bellows is surrounded by a confined volume, and it is evacuated by supplying oxygen to that confined volume, thus causing the bellows to collapse. A weight is provided in the free lower end of the bellows, so that upon release of the oxygen pressure in the confined area surrounding the bellows, the latter will automatically be exposed under the influence of the weight, thereby pushing the oxygen out from the confined area and through a mixing valve, wherein the oxygen is either vented to the atmosphere or mixed with a supply of room air and then injected into the expanding bellows for use in the next succeeding inhalation cycle. An inlet valve couples the mixing valve to the confined volume surrounding the bellows, and the inlet and outlet valves for the bellows apparatus are actuated alternately during the exhalation and inhalation cycles, respectively, by means of a logic circuit having its input coupled to one output of a master flip flop which in turn is controlled at one input by an exhalation timer signal and an automatic patient trigger signal, and controlled at its other input side by an inspiration timer signal, a pressure limit triggering circuit signal, and a volume limit signal coupled from the bellows apparatus.

The ventilator apparatus is provided with three different modes of operation selectable by means of a manually operable pneumatic switch. First, in an ASSIST mode the selecting switch is connected to activate the patient trigger circuit which, together with the pressure limit circuit, is responsive to the air pressure in a patient reference line, so that the master flip flop switches states to control the exhalation and respiration cycles of the bellows apparatus in accordance with the patient's breathing demands. That is, when the air pressure in the patient reference line drops to a low level indicating the completion of an inspiratory cycle, that low level pressure is detected by the patient trigger circuit which then triggers the master flip-flop to initiate the inspiratory cycle of the bellows apparatus. Then, during the ASSIST mode the pressure limit circuit provides a trigger signal to the master flip-flop to terminate the inspiratory cycle if the pressure in the patient reference line exceeds a predetermined value, while the volume limit detector device in the bellows apparatus also provides a trigger signal to the master flip-flop to terminate the inspiratory cycle after a predetermined maximum amount of air has been supplied to the patient from the bellows apparatus, or a fluidic timing device provides a trigger signal to the master flip-flop to terminate the inspiratory cycle after a predetermined amount of time. Therefore, the first one of the pressure, volume, or time signals to reach its predetermined maximum value is the signal which triggers the flip-flop to terminate the inspiration cycle; and the command from the patient trigger circuit terminates the exhalation cycle.

When the manually operable mode switch is positioned to select a CONTROL mode, the exhalation timer is activated and the patient trigger circuit is deactivated, so that the master flip flop is controlled at one input by the output of the exhalation timer, while it is controlled at its other input by the pressure limit circuit, the inspiration timer, and the volume limit detector. Accordingly, in the CONTROL mode the exhalation cycle is automatically timed, as is the inspiration cycle, but the latter is also terminated prematurely of the inspiration timer output if the pressure limit signal or volume limit signal reach their predetermined maximum values.

The bellows for supplying air to the patient has an adjustable volume which is determined by a movable plate positioned to control the expansion of the bellows and which also contributes to defining the confined volume surrounding the bellows. During the inspiration cycle, the master flip flop controls a power valve which supplies oxygen under pressure to the confined volume thereby causing contraction of the bellows. Then, upon releasing the pressure in the confined volume, the bellows starts to expand under the force of a weight carried therein and the oxygen is forced out of the confined area and through the inlet valve which is actuated to an open condition by the logic circuit. A mixing valve which receives the oxygen from the inlet valve is adjustable to conduct a controlled amount of the oxygen through to the bellows along with a partial supply of filtered room air. The room air is received at ambient pressure and is drawn into the bellows due to a vacuum caused by its expansion. However, the oxygen is supplied under pressure as a result of its forced expulsion from the confined area so that the mixing valve permits the oxygen content of the gas supplied to the bellows to be varied from 21 - 100%.

Each of the timer devices comprises a bellows housed within a chamber having an input orifice for receiving oxygen at a predetermined pressure to cause a timed contraction of the bellows. A shaft has one end fixed to the movable end of the bellows, while the opposite end of the shaft closes a vent on a back pressure detector which is coupled to the input of the master flip-flop. Therefore, a pair of opposed inputs to the master flip-flop are controlled respectively by the movable shafts on the two timer bellows. Futhermore, each of the chambers surrounding the timer bellows have dump valves mounted therein, such valves being actuable by opposed outputs of the master flip-flop, so that as soon as the back pressure detector of one of the bellows provides an output for switching the master flip-flop, the resultant output of the flip-flop is coupled back to that bellows chamber to cause its depressurization, and to prepare it for its next timing cycle. The two bellows devices and their surrounding chambers are mounted side by side and their back pressure sensing elements are movably mounted on springs, so that they are adjustably positioned by means of a pair of cams fixed on a shaft, so that rotation of the shaft causes movement of the cams and adjustable movement of the two sensing devices. Thus, this movement of the sensing devices changes the timing periods for both the exhalation and inspiration timers which can be adjusted in unison by rotation of the shaft. Furthermore, a by-pass valve is provided in parallel with the input orifice to the inspiration timer, and that by-pass valve can be opened to decrease the inspiration time, thus adjusting the inspiration/exhalation (I/E time ratio. However, the timing devices are constructed so that the I/E ratio has a maximum value of unity.

The patient trigger circuitry, and the pressure limit circuit have identical configurations, and each comprises a more universal trigger circuit for automatic operation in a patient ventilator. In particular, the universal trigger circuit consists of a six-gate fluidic circuit having three proportional amplifiers connected in series with each other and with three serially connected fluidic flip-flops. In accordance with the invention the universal circuit can be used as the patient trigger and the pressure limit circuit as described above, and depending on the input connections thereto it can function to provide an output in response to a small differential pressure at its inputs; it can function to provide an output in response to pressures slightly below ambient, as would be caused by a patient's breathing efforts; it can function to provide an output in response to pressure levels above or below atmospheric, wherein the device is automatically biased so that it can be used in conjunction with end expiratory pressure signals; it can function to provide an output in response to air pressure inputs indicating maximum levels; and it can function to provide an output in response to flow signals, or rate of change of pressure as is sometimes desirable.

In accordance with the use of the universal trigger circuits, as controlled in part by end expiratory pressure signals, the circuit is utilized to provide an output in response to small differential pressures. To allow the Positive End Expiratory Pressures (PEEP) to be used during assisted breathing, without the need for the patient's inhalation effort to return the patient hose to ambient pressure, the PEEP pressure is fed through a diaphragm valve to the patient trigger module, to bias that module so that it can be triggered while the patient reference line is still above the ambient pressure level.

BRIEF DESCRIPTION OF THE DRAWINGS

One embodiment of the invention is described herein in conjunction in the accompanying drawings. In such drawings.

Figure 1:
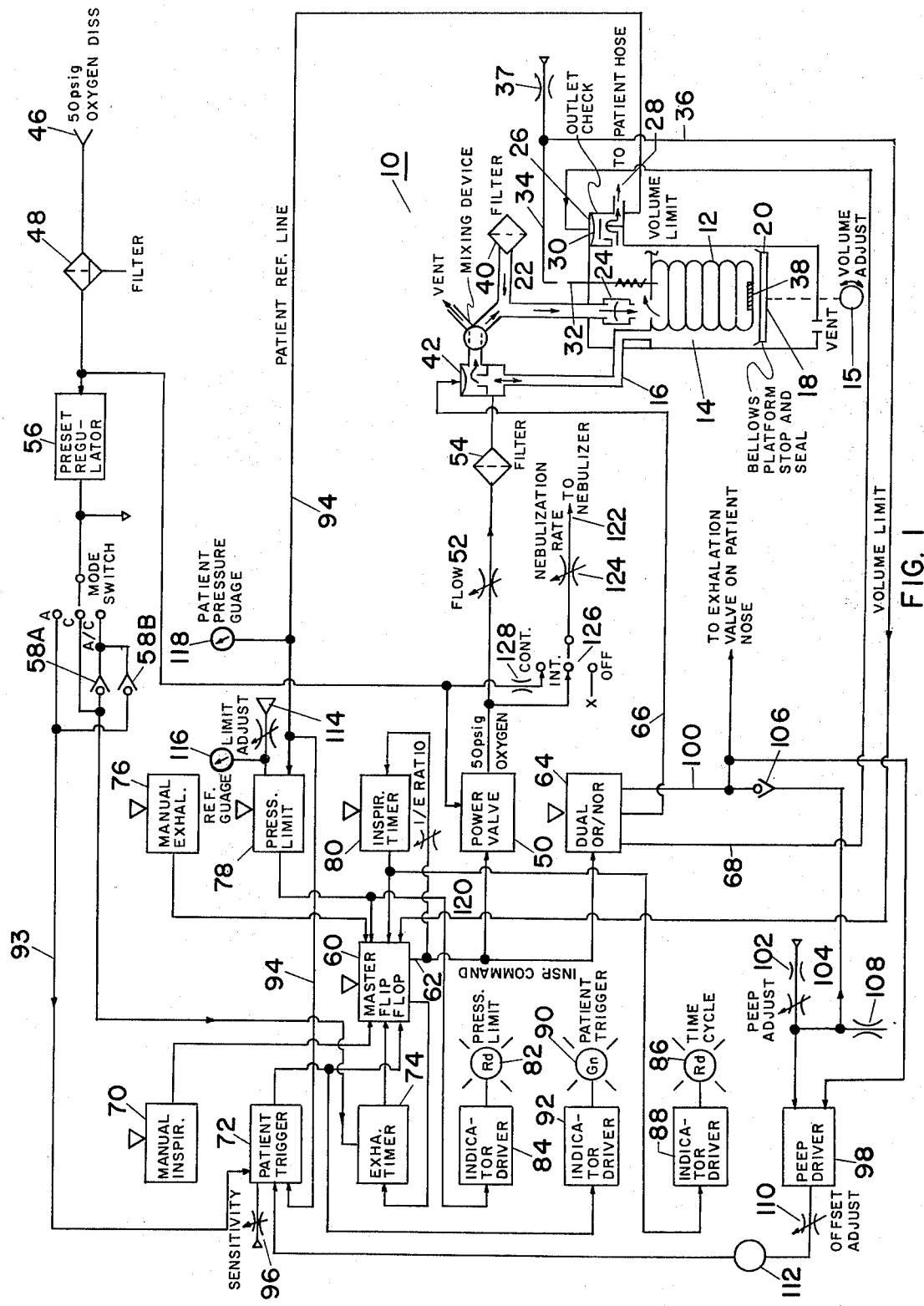
FIG. 1 shows a block diagram of a patient ventilator apparatus according to the invention.

DETAILED DESCRIPTION OF AN EMBODIMENT OF THE INVENTION:

An embodiment of the invention is depicted in block diagram form in FIG. 1 of the drawings, and includes a bellows apparatus 10 having a bellows element 12 fixedly held at its upper end within a cylindrically formed chamber 14. The chamber 14 is provided at its upper end with a connecting conduit 16, and is provided at its lower end with an adjustable plate 18 having a seal 20 connected at its periphery for sealing the plate against the sidewalls of the chamber 14. The plate is adjustably movable through the chamber 14 by means of an adjusting device 15, so that when the plate is moved upwardly the confined volume of the chamber within which the bellows can expand and contract is decreased, while such volume is increased when the plate 18 is moved downwardly within the chamber 14. In operation, the bellows element 12 is charged with air through an input duct 22 having a check valve 24 mounted thereon, and the bellows element is connected in communication with an outlet valve 26 for actuation to allow air within the bellows element to be discharged to the patient during the inspiration cycle. The discharge of air from the bellows element 12 is effected by pressurizing the chamber 14 with oxygen supplied through the conduit 16. When the chamber 14 is so pressurized with oxygen, it causes the bellows element 12 to collapse to expel the air previously charged therein.

Accordingly, the tidal volume of the system is determined by the placement of the plate 18 which plate also minimizes gas consumption by limiting the confined volume surrounding the bellows element 12. As illustrated, the check valve 24 closes off the input port to the bellows element during its collapse. The output valve 26 also includes a check valve to prevent air from the patient hose 28 from being injected into the bellows element, and the valve 26 is controlled by a diaphragm 30, which in turn is controlled by the fluidic circuitry described below.

The bellows element 12 continues its collapsing movement until the chamber 14 is depressurized in response to one of four different control signals which are adapted to terminate the inspiration cycle. One of these four control signals is initiated by a rod 32 mounted above the bellows element 12 and spring loaded in a downward direction, but movable upwardly due to pressure exerted by the upward movement of the lower portion of the bellows element wherein such upward movement of the rod indicates the total exhaustion of the air previously charged into the bellows element. The rod 32 closes a vent in a pressurized conduit 34, thus providing a back pressure signal along a volume limit conduit 36. The conduit 34 is pressurized by a regulated supply of oxygen fed through an orifice 37.

As stated above, the inspiration cycle is terminated when the chamber 14 is depressurized, and at that time the bellows element 12 automatically expands under the force of a weight 38 housed in its lower extremity. As the bellows element expands it creates a partial vacuum which opens the inlet check valve 24 and draws air inwardly through the conduit 22 which has a filter 40 connected thereto and disposed in communication with room air. Depressurization of the chamber 14 is obtained by opening a bellows inlet valve 42 so that the oxygen which is forced out of the chamber 14 by the expanding bellows element 12 is coupled through the inlet valve 42 to a three port mixing valve 44 as described in detail below in conjunction with FIGS. 3–7. In operation, the oxygen discharged from the chamber 14 through the valve 42 is vented to atmosphere by the valve 44, or is directed in an adjustably controlled volume to the conduit 22 which supplies air to the bellows element 12. Since the oxygen is discharged under pressure from the chamber 14, due to the expansion of the bellows element 12, the pressure of the oxygen exiting the mixer valve 44 is greater than the ambient pressure of the room air coupled through the filter 40, and therefore the oxygen/air mixture can be varied by positioning the valve 44 to a desired position.

The input and output valves 26 and 42 of the bellows apparatus 10, and the supply of oxygen to the chamber 14, are controlled by the fluidic circuitry shown in block diagram form in FIG. 1, such circuitry being energized by a 50 psig oxygen supply source indicated at reference numeral 46. The pressurized oxygen is coupled through a filter 48 to a power valve 50 which is gated to supply oxygen through an adjustable flow valve 52, and through a silencer-filter 54 to the input conduit 16 for the bellows chamber 14. The output of the filter 42 is also coupled to a regulator 56 wherein the oxygen pressure is reduced so that the oxygen emanating from the regulator 56 can be used as a supply source for the active elements of the fluidic circuitry. The regulated oxygen, which may be at a pressure of about 5 psig, is also coupled through a three position mode selector switch 58, which permits the selection of three modes of operation, including an ASSIST mode, a CONTROL mode, and an ASSIST/CONTROL mode.

The fluidic circuitry includes a master flip flop 60 having a principle output 62 which actuates the power valve 50, and which operates a dual OR/NOR circuit 64 to provide regulated oxygen pressure signals along he respective conduits 66 and 68 to the inlet and outlet valves 42 and 26 of the bellows apparatus 10. In particular, when the output 62 of the flip flop 60 provides a positive pressure, the dual OR/NOR circuit provides a positive signal on the output conduit 66 to close the inlet port to the bellows apparatus, while the outlet port 26 is allowed to open so that the inspiration cycle will commence due to collapsing movement of the bellows element 12, which in turn results from pressurization of the chamber 14. Similarly, upon completion of the inspiration cycle, the flip flop 60 will switch to its opposite stable state whereby a positive regulated pressure signal will be coupled along conduit 68 to close the outlet valve 26 while the pressure on conduit 66 will be decreased to allow the valve 42 to open so that the oxygen discharged from the bellows chamber 14 will pass through that input valve 42 to the mixing valve 44.

The flip flop 60 has three inputs which cause it to switch to its inspiration command state wherein it provides an output or conduit 62, and those three inputs are supplied from a manually operable input signal device 70, a patient trigger device 72, and an exhalation timer device 74. On the other hand, the flip flop has four inputs for causing it to terminate its inspiration command, and those inputs are coupled from a manually operable exhalation triggering device 76, a pressure limit circuit 78, an inspiration timer device 80, and the volume limit detector device formed by the elements 32, 34, and 36 disposed in the bellows apparatus 10. A pressure limit display device 82 is actuable to exhibit a red display in response to an indicator signal from a driver device 84 which in turn is energized by the output of the pressure limit circuit 78. The display device 82 utilizes reflected light. Similarly, a red display device 86 is operated by a driver 88 in response to an output from the inspiration timer 80, while a green display light 90 operates in a similar manner under the control of an indicator driver 92 which is energized by an output from the patent trigger circuit 72.

In the operation of the circuitry, when the ASSIST mode is selected, a regulated oxygen pressure signal is applied to the patient trigger circuit through a conduit 93 to put it in an energized condition, and an input control port for the patient trigger circuit is coupled through a patient reference line 94 to the patient hose line 28, so that the patient trigger circuit provides output to switch the master flip flop 60 to its inspiration state when the pressure in the patient reference line 94 decreases to a minimum indicating the completion of an exhalation cycle. While the system is operating in its ASSIST mode, the green light 90 will be actuated at each instance of a patient trigger output signal, which in turn is controlled by the patients breathing in response to a signal coupled along the patient reference line 94.

An additional input to the patient trigger device 72 includes a regulated oxygen signal coupled through an adjustable input port 96 to control the sensitivity of the trigger device 72, and in input signal from a Positive End Expiratory Pressure (PEEP) 98, wherein the patient trigger device 72 is adaptable to provide an output in response to a small differential input pressure between the input coupled along the conduit 94 and the PEEP input. The PEEP circuit 98 has a gate input coupled from an output conduit 100 of the dual OR/NOR circuit 64, and the gate is maintained in a closed condition by the positive regulated oxygen supply coupled through a small orifice 102, an adjustable orifice 104, and a one way valve 106, to the gate input, wherein the junction of the adjustable orifice 104 and the one way valve 106 are vented to the atmosphere through an orifice 108. However, during an exhalation cycle, the pressure in the conduit 100 opens the PEEP driver circuit to permit the regulated pressure coupled through the orifices 102 and 104 to be applied through an offset adjust orifice 110 and a spike - damping volumetric chamber 112 to the patient trigger device 72.

The pressure limit circuit is identical in construction to the patient trigger circuit, but provides an output in response to a high pressure sensed on the patient reference line 94, and the sensitivity of the device is adjustable by means of a variable orifice 114 coupled as a second input thereto. Also, a pressure gauge 116 is connected at the second input to the pressure limit circuit 78 for displaying the selected pressure limit adjustment to which the circuit is sensitive, and a second pressure gauge 118 is connected to the patient reference line so that the actual pressure such line can be monitored. An adjustment is provided but not shown in FIG. 1 wherein the periods of the exhalation timer and the inspiration timer can be simultaneously adjusted, and an adjustable orifice 120 is provided in the input line to the inspiration timer, so that the inspiration/exhalation (I/E) ratio can be adjusted. These adjustments are desireable since medical ventilation systems require a matching of the I/E ratio to the needs of individual patents, and since it is usually considered detremental to use I/E which is greater than unity. Also, controlled breathing requires uniform cycle rates, but such rates should be adjustable to permit changes in the minute-volume, without disturbing the selected I/E ratio. The above-mentioned controls satisfy these requirements.

An additional function of the ventilator apparatus disclosed herein is provided by a conduit 122 for coupling to a nebulizer device wherein that conduit 122 is connected through an adjustable orifice 124 to an OFF position, an INTERMITTENT position wherein the nebulizer is operated by the output of the power valve 50, and a CONTINUOUS position wherein the nebulizer is operated by the supply source of oxygen as coupled through an orifice 128.

In summary, in the ASSIST mode the inspiration cycle is terminated by the pressure limit circuit 78, by the manually operable signal device 76, by the volume limit signal coupled along the conduit 36, or by the inspiration timer 80, and the exhalation cycle is terminated by the patient trigger circuit 72, or the manually operable signal device 70.

In the CONTROL mode the regulated oxygen supply is coupled through the selecting switch 58 to energize the exhalation timer, while the patient trigger circuit 72 is deenergized. Therefore, in the CONTROL mode the inspiratory command generated in the conduit 62 is initiated by the exhalation timer 74 or the manual signal device 70, while the inspiratory cycle is terminated by any one of the four inputs to the master flip-flop 60 from the manually operable device, such inputs including signal pressure limit circuit 78, the inspiratory timer 80, or the volume limit signal conducted along conduit 36. During normal operation of the CONTROL mode, the master flip-flop may be operated during both the inspiratory and exhalation cycles in a timed manner determined by the timers 74 and 80, respectively. However, the inspiratory cycle is terminated prematurely of its timed duration if either pressure limit or the volume limit exceeds its timed predetermined value.

Then, in the ASSIST/CONTROL mode, the selector switch 58 energizes both the patient trigger circuit 72 and the exhalation timer 74 through the use of a pair of one way valves 58A and 58B, so that the circuitry operates as described above with respect to the CONTROL mode with the exception that flip-flop 60 will be triggered to generate its inspiratory command along conduit 62 by the patient trigger signal from the device 72, as well as by the exhalation timer 74.

Figure 2:
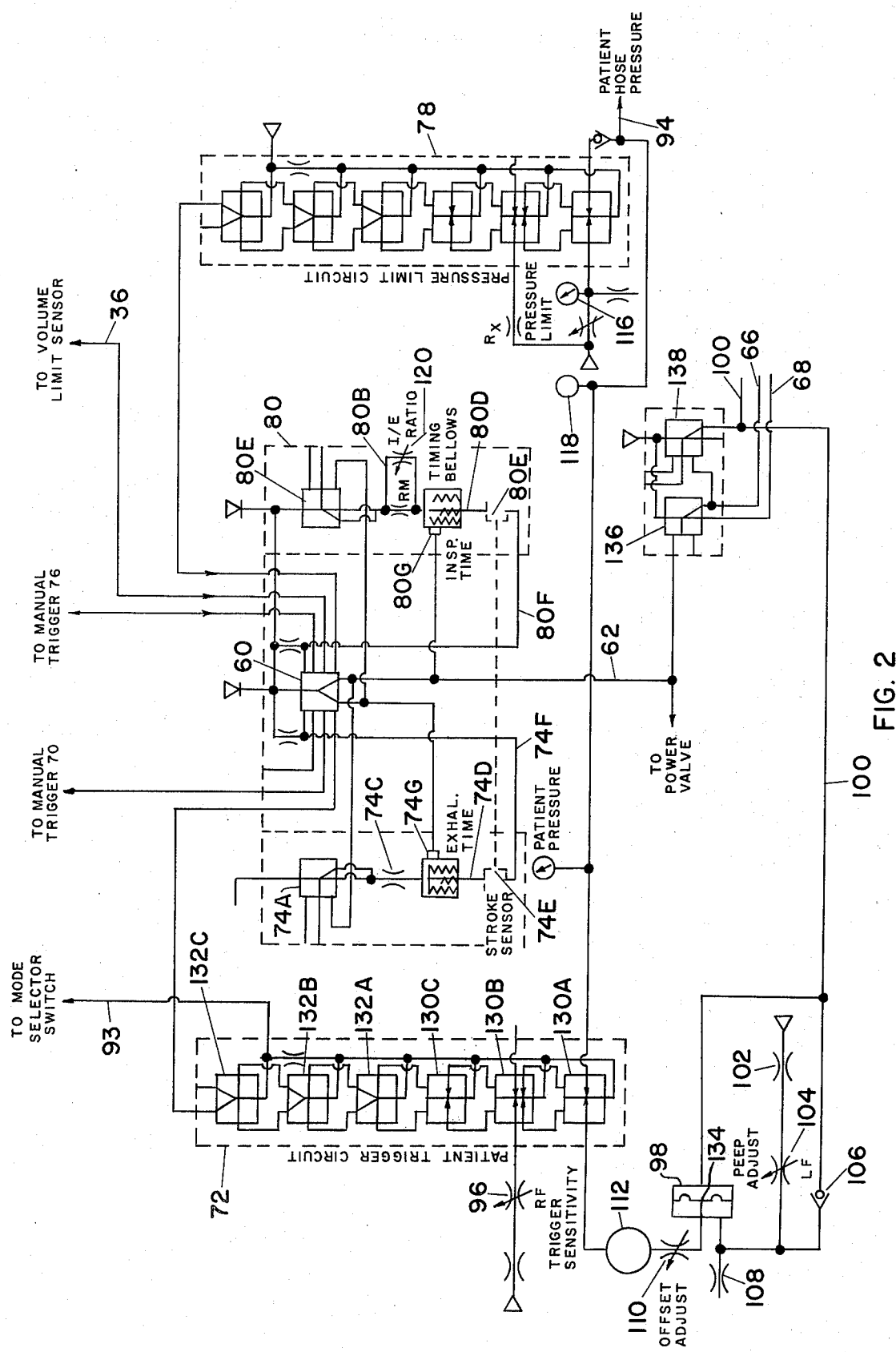
FIG. 2 is a schematic view of the fluidic circuitry illustrated in FIG. 1.

The actual circuitry included in the blocks of FIG. 1 is shown in greater detail in FIG. 2, wherein a preferred form of the patient trigger circuit 72 is shown as comprising a six section fluidic device incorporating three proportional amplifiers 130A, 130B, 130C, connected in series with each other and in series with three serially connected flip flops 132A, 132B, 132C. Each of the six circuits has its supply input coupled along the conduit 73 to the mode selector switch 58 while each of circuits 130B, 130C, 132A, 132B, and 132C, have their control inputs coupled to the respective outputs of the preceeding stage; while the control inputs to the first proportional amplifier 130A are coupled respectively to the output of the PEEP circuit 98 and to the patient reference line 94. Furthermore, the adjustable sensitivity orifice 96 is coupled to a second control input to the proportional amplifier 130B, and this configuration permits a stable sensitivity adjustment from +1 to more than −10 cm $H_2O$ with respect to ambient pressure. The fourth input to the amplifier 130B is vented. The gating device for the PEEP driver 98 which is shown schematically in FIG. 2 comprises a diaphragm 134 which closes off the conduit leading to the PEEP input for the proportional amplifier 130A, and it is seen that the PEEP driver 98 is maintained in a closed condition by that diaphragm 134 due to pressure from conduit 100 during inspiration. The pressure through the one way valve 106 is negated by a signal from the dual OR/NOR circuit 17 during the inspiration cycle. Diaphragm 134 permits oxygen flow from the valves 102 and 104 and then through the adjustable valve 110 and the damping chamber 112 through to the proportional amplifier 130A during exhalation. Also, during exhalation the pressure through 106 is delivered to conduit 100 where it is used to hold the patient circuit exhalation valve at the PEEP pressure.

In operation, an end expiratory pressure which remains higher than ambient pressure is generated by bleeding a small amount of the driving gas into the exhalation exhaust line through the one way valve 106. This keeps the diaphragm 134 of the PEEP device 98 at a slight positive pressure. Then, since most exhalation valves hold patient hose pressures slightly higher than their actuation pressures, the OR/NOR output pressure with PEEP will usually be less than the PEEP pressure shown on the patient pressure gauge. Therefore, variations in the obtainable PEEP pressures will be experienced with exhalation manifolds of different manufacturers. To allow PEEP to be used during assisted breathing, without the need for the patient's inhalation effort to return the patient hose to ambient conditions, the PEEP pressure is fed to the patient trigger module to bias that module so that it can be triggered while the patient hose pressure is still above the ambient pressure level. The amount of pressure difference required to switch the trigger module is preset by the offset-adjust valve 110. During inspiration, the diaphragm 134 is closed to remove the bias signal from the patient trigger module so that high exhalation valve pressures will not hold the ventilator in an inspiration condition. However, during exhalation, the diaphragm 134 opens and allows the PEEP pressure to reach the patient trigger module circuit 130A. The system is usually preset so that the pressure difference required to trigger the patient trigger module is relatively large as compared to that normally required without PEEP to compensate for leaks. The offset-adjust valve 110 is provided to function as a leak compensator for desensitizing the patient trigger module during PEEP operation.

The pressure limit circuit 78 is identical to the above-described patient trigger circuit 72 in its construction, with the exception that the source supplied for each of the six individual circuits is coupled to the regulated source of oxygen provided at the output of the regulator 56, while the control inputs to the pressure limit circuit 78 are as described above in conjunction with FIG. 1.

It is seen, therefore, that the circuits 72 and 78 as illustrated in FIG. 2 of the drawings are identical, although their input signals may be connected in different ways to make the circuit responsive to different input parameters. In addition to the responses described above with respect to FIG. 2 of the drawings, the inputs to the six-state circuit can be coupled in at least three different configurations so that the circuit may be described as a universal trigger circuit. In this regard, for example, the inputs can be connected as illustrated at 72 in FIG. 2, while the PEEP input is replaced by an ambient pressure input so that the circuit will be sensitive to small negative pressures. As another example, the PEEP input to the circuit 72 as illustrated in FIG. 2 may be connected to be automatically biased to allow triggering at pressure levels above or below atmospheric pressure. For example, the input may be connected to a three-position switch so that when PEEP pressures are used, a pressure slightly above atmospheric is applied, while with negative end-expiratory pressures (NEEP), a pressure slightly below atmospheric is applicable through a second position of the switch. In such NEEP applications, the reference-adjust gas is used to drive a venturi for evacuating the patient hose, thereby generating the vacuum necessary for the negative bias. The third position of the switch may provide for normal operation so that the universal trigger circuit may be switched from NORMAL, to PEEP, to NEEP without requiring readjustment of the sensitivity control. A further example of the responsiveness of the universal circuit results when a suitable restriction is placed in the patient hose input, while a feedback connection is coupled to the circuit 72 in place of the PEEP input so that the ventilator will be cycled as a function of flow, or as a function of the rate of change of pressure. That is, the feedback connection can be used to sense flow since the pressure differential across the restriction in the patient hose will give an indication of such flow. This last-described configuration can be used to turn on the ventilator due to a slight patient breathing effort, and if a time delay circuit such as a fluidic RC circuit is provided in a parallel feedback line, the patient trigger signal can be extended.

The OR/NOR circuit 64 is also depicted in schematic form in FIG. 2 and comprises a two stage device, wherein the first stage 136 provides a positive pressure output along the conduit 66 in response to an input signal received from the flip flop 60 along the conduit 62. Similarly, the second stage 138 provides an output along conduit 100 during the inspiration cycle to maintain the exhalation valve on the patient hose in a closed condition during such inspiration cycle.

In the past, fluidic timers for respiratory equipment have been constructed to allow a certain volume (capacitance) of fluid to slowly increase or decrease to a desired switching pressure level. However, it is difficult to repeat such pressures, and elaborate circuitry is usually required to provide the necessary repeatability. Another type of known timer comprises a fluidic oscillator combined with complex digital counter stages, and this configuration also has obvious drawbacks.

In the present invention accurate and relatively simple timers are provided wherein each of the timing devices 74 and 80 comprises a logic circuit 74A and 80A, and a bellows device 74B and 80B, respectively. When the flip flop 60 is switched to provide an inspiration command along the conduit 62 the logic circuit 74A provides a regulated pressure output coupled through an orifice 74C to the chamber of the bellows device 74B, and causes the bellows element thereof to collapse. A rod 74D is fixed to the moveable portion of the bellows element, and is mounted to engage a sensor 74E for causing a back pressure along a conduit 74F which is connected as an inspiration cycle terminating signal of the flip flop 60. Similarly, the timing device 80 has the input of its logic circuit 80A connected for actuation by the opposing output of the flip flop 60 while the sensor device 80E couples a signal along the conduit 80F to terminate the exhalation cycle of the apparatus by switching the flip flop 60. Additionally, the adjustable orifice 120 is connected in parallel with the orifice 80C to vary the I/E ratio as described above.

Figure 3:
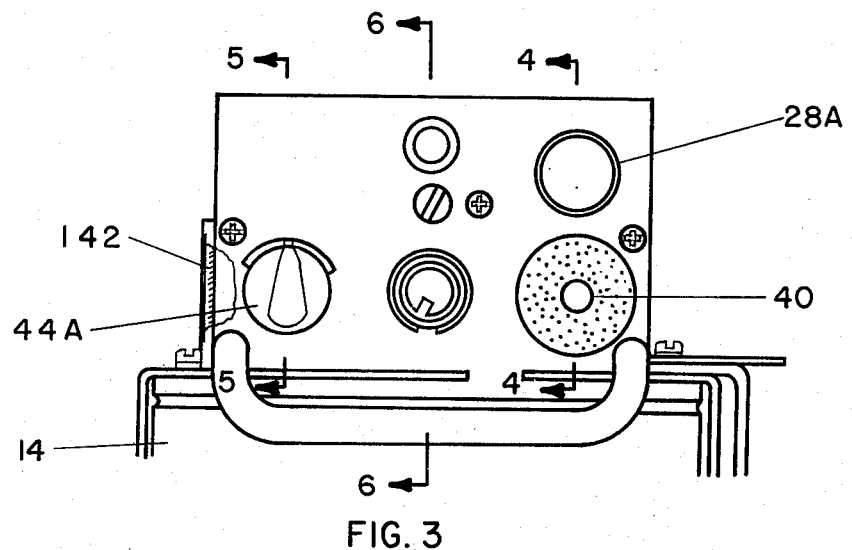
FIG. 3 is a front elevation of the mixing device mounted on the bellows apparatus disclosed in FIG. 1.
Figure 4:
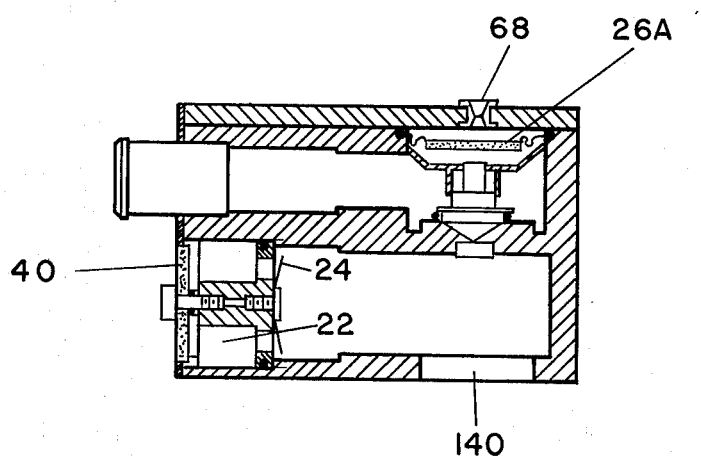
FIG. 4 is a sectional view taken along the line 4—4 of FIG. 3.
Figure 5:
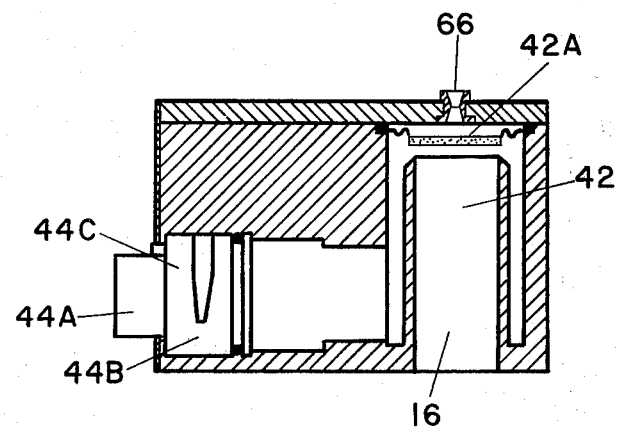
FIG. 5 is a sectional view taken along the line 5—5 of FIG. 3.
Figure 6:
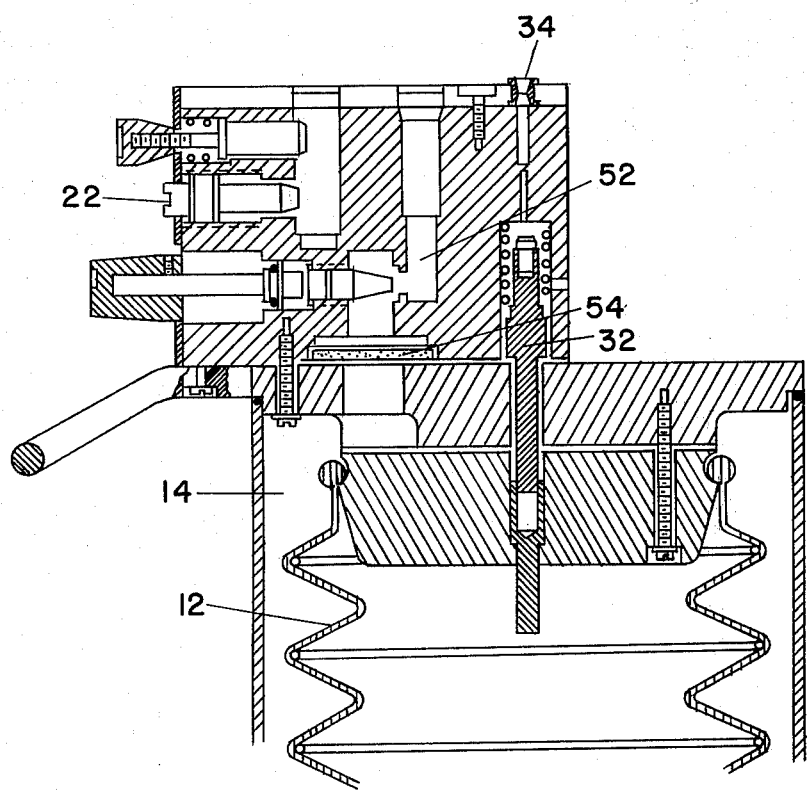
FIG. 6 is a sectional view taken along the lines 6—6 of FIG. 3.

Various additional details of the construction of the valving apparatus are shown in FIGS. 3–7. Particularly, FIG. 3 shows an embodiment of the valve construction utilized with the bellows apparatus 10 wherein the room air is drawn through the filter 40, the oxygen/air mixture is controlled by the valve knob 44A, and the patient output hose is connected to the output port 28A. The internal configuration of the valve apparatus is shown in FIGS. 4–6 which comprise sectional views wherein the opening 140, as shown in FIG. 4, comprises the port opening of the bellows element 12, while the input check valve 24 is shown in communication with a duct 22 corresponding with the duct 22 illustrated in FIGS. 5 and 6. Similarly, the air filter 40 is also shown in FIG. 4, and the duct 16, communicating with the bellows chamber 14 and valve 42, is shown in FIG. 5. Also, the adjustable flow control orifice 52, and the oxygen filter 54 are shown in FIG. 6, while the valve stem for the mixing valve 44 is shown as element 44B in FIGS. 5 and 7. When the valve stem 44B is rotated by means of the valve knob 44A to its extreme counter-clockwise position, all of the oxygen forced out of the chamber 14 by the expanding bellows element 12 is vented to the atmosphere through a vent opening 142 as illustrated in FIG. 3. As the knob 44A is rotated clockwise, however, increasing quantities of oxygen are permitted to flow through the conduit 22, first through a slit portion 44C in the valve stem 44B, and then through the full open orifice 44D thereof so that when the valve knob 44A is turned completely clockwise, the entire quantity of oxygen forced out of the chamber 14 is drawn into the bellows element 12. The bladder elements 26A and 42A shown respectively in FIGS. 4 and 5 are controlled by the pressure signals coupled through conduits 68 and 66, respectively, as described above in conjunction with FIG. 1.

Since the oxygen/air mixture is effected by the expanding bellows, and proportioned by the valve 44, the oxygen concentration is unaffected by the patient's breathing, the inspiratory flow rate, the tidal volume, the patient hose pressure, or the cycle time, thereby providing an accurately controllable system in this regard.

Figure 8:
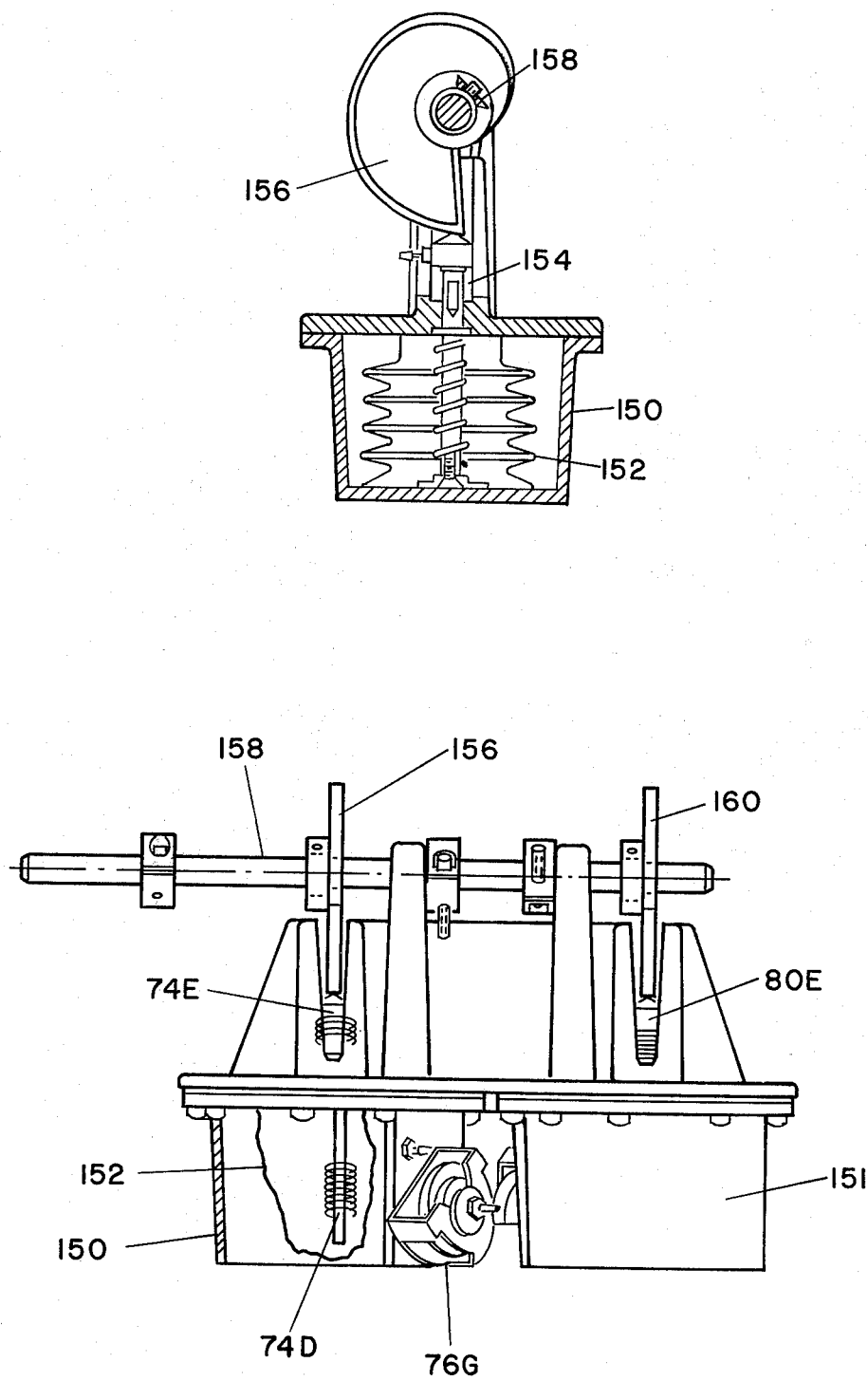
FIG. 8 is a sectional view of the timer devices illustrated schematically in FIG. 2.
Figure 7:
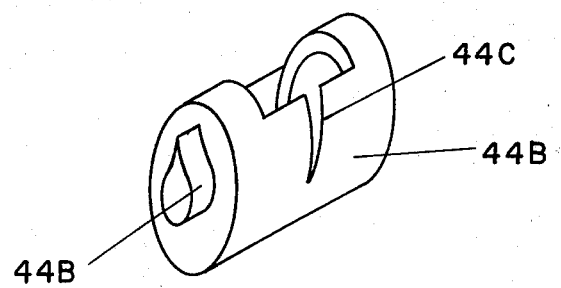
FIG. 7 is a perspective view of the mixer valve stem illustrated in FIGS. 3–5.

The timing devices 74B and 80B, shown schematically in FIG. 2, are illustrated in FIG. 8, wherein the device 74B, is depicted in a partially sectional view. The timing devices include sealed cannisters 150, 151, each having a sealed collapsible bellows device 152 mounted therein. As shown, the sensor device 74E is supported on a spring 154 and its elevation position is determined by the pressure exerted thereon by a cam 156 mounted on a shaft 158. Similarly, the sensor device 80E is positioned by a corresponding cam 160 mounted on the shaft 158. In the operation of the timers, a regulated air pressure is selectively applied through one of the orifices 74C and 80C to the cannisters 150 and 151. Then, for example, if the cannister 150 is charged, the bellows 152 will collapse causing the springloaded rod 74D attached thereto to move upwardly until it engages the sensor 74E, thus closing a vent in the line 74F so that the flip flop 60 receives an input signal for switching it to provide an inspiratory command along conduit 62 as shown in FIGS. 1 and 2. The bellows 152 and the spring loading on the rod 74D are so proportioned that the movement of the rod does not require a large pressure change, so that the travel time for the rod can be accurately established. During calibration procedures, the adjustable orifice 120, as shown in FIGS. 1 and 2 is completely closed, whereupon the cams 156 and 160 are adjusted to provide the necessary exhalation and inspiratory time periods so that the desired maximum value for the quantity I/E is defined. Then, the timing periods for both of the timers 74B and 80B can be simultaneously adjusted by rotating the shaft 158 to reposition the sensing devices 74E and 80E by means of the cams 156 and 160. Subsequently, the I/E ratio can be decreased by opening the valve 120 to a desired position.

Figure 9:
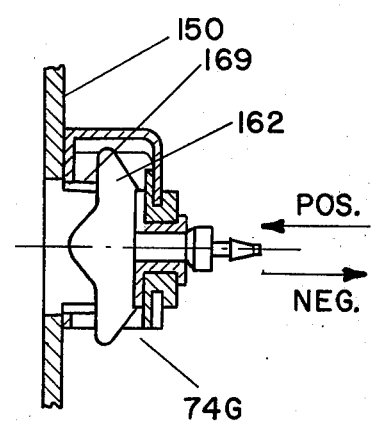
FIG. 9 is a sectional view of a dump valve used with the timer devices of FIG. 4.

The dump valves described above in conjunction with FIG. 2, are shown in FIG. 8, and a sectional view of the dump valve 74G is illustrated in FIG. 9 wherein it is seen that a bladder 162 maintains a valve seat 164 in a closed position on a discharge opening in the side wall of the cannister 150. Then, when the master flip flop is actuated by the exhalation timer 74 to provide an inspiratory command along the output conduit 62, the opposing output of the flip flop 60 is coupled to the bladder 162 to provide a slight negative pressure thereto so that the oxygen stored in the timer cannister 150 is exhausted to the atmosphere through the port 166 by the released valve seat 164.

The dump valve seals the outlet opening in the cannister 150 when the flip flop is switched out of its inspiratory command state.

In summary, the apparatus disclosed in the foregoing specification, and in the accompanying drawings, provides a patient ventilator which is controlled solely by fluidic circuitry to function manually, automatically, or semiautomatically, in response to the breathing requirements of a patient.

What is claimed is:

1. A patient trigger circuit for use in a ventilator apparatus comprising first, second, and third fluidic circuits each consisting of a proportional amplifier, and fourth, fifth and sixth fluidic circuits each consisting of a flip flop circuit, each said fluidic circuit having a pair of input ports and a pair of output ports, wherein the output ports of said first through fifth fluidic circuits are connected to the input ports of the next succeeding circuit; the output ports of said sixth fluidic circuit provide trigger circuit output signals; one of said input ports of said first fluidic circuit is connected to a source of control input signals; and the other input port of said first fluidic circuit is connected to a source of reference signals; and wherein said second fluidic circuit includes a second pair of input ports for connection respectively to a source of reference bias pressure, and to a source of sensitivity signals.

* * * * *